United States Patent
Emslie et al.

(10) Patent No.: US 7,347,991 B2
(45) Date of Patent: *Mar. 25, 2008

(54) STICK COMPOSITIONS

(75) Inventors: Bruce Steven Emslie, Wirral (GB); Kevin Ronald Franklin, Wirral (GB); Neil Robert Fletcher, Wirral (GB)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 745 days.

This patent is subject to a terminal disclaimer.

(21) Appl. No.: 10/842,136

(22) Filed: May 10, 2004

(65) Prior Publication Data

US 2004/0223995 A1    Nov. 11, 2004

(30) Foreign Application Priority Data

May 10, 2003    (GB) ................... 0310769.5

(51) Int. Cl.
*A61Q 15/00* (2006.01)
*A61K 8/02* (2006.01)

(52) U.S. Cl. .................. 424/65; 424/400; 424/401

(58) Field of Classification Search .......... 424/65, 424/400, 401

See application file for complete search history.

(56) References Cited

U.S. PATENT DOCUMENTS

| | | | |
|---|---|---|---|
| 3,969,087 A | 7/1976 | Saito et al. | 44/7 |
| 5,429,816 A | 7/1995 | Hofrichter et al. | 424/66 |
| 5,650,144 A | 7/1997 | Hofrichter et al. | 424/66 |
| 5,840,286 A | 11/1998 | Gardlik et al. | 424/65 |
| 5,840,287 A | 11/1998 | Guskey et al. | 424/65 |
| 6,241,976 B1 | 6/2001 | Esser et al. | 424/65 |
| 6,287,544 B1 | 9/2001 | Franklin et al. | 424/65 |
| 2002/0159961 A1 | 10/2002 | Yamato et al. | 424/65 |

FOREIGN PATENT DOCUMENTS

| | | |
|---|---|---|
| WO | 93/23008 | 11/1993 |
| WO | 03/005977 | 1/2003 |

OTHER PUBLICATIONS

Co-pending: Applicant: Emslie et al., U.S. Appl. No. 10/842,094, filed May 10, 2004.
Co-pending: Applicant: Emslie et al., U.S. Appl. No. 10/842,137, filed May 10, 2004.
PCT International Search Report in a PCT application PCT/EP 2004/004507.
GB Search Report in a GB application GB 0310771.1.
PCT International Search Report in a PCT application PCT/EP 2004/004512.
PCT International Search Report in a PCT application PCT/EP 2004/004514.

*Primary Examiner*—Shelley A. Dodson
(74) *Attorney, Agent, or Firm*—Karen E. Klumas

(57) ABSTRACT

Anhydrous cosmetic stick compositions containing a continuous phase of a water-immiscible cosmetic oil structured by a fibre-forming amido structurant and containing a suspended particulate antiperspirant or deodorant can suffer from either somewhat poor physical stability when formed, or preparative difficulties using conventional processes for making stick compositions or opaqueness. The problem can be ameliorated or overcome by the use of a combination of amido structurants comprising (i) an N-acylaminoacid amide in which the N-acyl substituent has the formula —CO—$R^x$ in which $R^x$ represents a branched $C_6$ to $C_{11}$ alkyl group in combination with a further amido structurant (ii), selected from (iia) N-acylaminoacid amides other than (i), (iib) cyclodipeptides and (iic) a 1,2-di amido-substituted cyclohexane.

57 Claims, No Drawings

STICK COMPOSITIONS

The present invention relates to stick compositions and in particular to such compositions containing a suspended antiperspirant or deodorant, and a carrier material therefore comprising a cosmetically acceptable water-immiscible oil that is solidified by an amido-substituted amino acid, which compositions are at least translucent, and to their preparation and use.

TECHNICAL FIELD BACKGROUND AND PRIOR ART

Cosmetic antiperspirant formulations are known and available to the public in several different physical forms for application using the corresponding type of applicator, including dispensers for powder mixes, foams, gelled or thickened liquids, liquids of low viscosity that can be sprayed, aerosol formulations, creams, soft solids and sticks. The preferred choice of physical form can often depend on the history of product, and local preferences, which may themselves vary over time as fashions change. One physical form which has been popular especially in North America for antiperspirant and deodorant compositions during the last twenty years is that of sticks. The term "stick" herein is employed in its natural meaning, that is to say a material that is firm to the touch, is often in the shape of a rod or bar and commonly is housed in a container comprising a barrel having an open end and an opposed piston which can be slid up the barrel to expel the stick, which retains its shape and integrity during its expulsion.

Cosmetic antiperspirant sticks typically comprise an antiperspirant active that is dissolved or suspended in a cosmetically acceptable carrier material of which at least a fraction is a cosmetically acceptable water-immiscible oil. In one highly desirable class of cosmetic sticks, the carrier material comprises either no polar liquid or no more than the proportion that can form a single liquid phase with the water-immiscible oil or oil mixture.

One class of material that has hitherto been proposed for solidifying water-immiscible oils comprises non-polymeric fibre-forming structurants. A number of such structurants comprise alkyl ester derivatives of certain saccharides, such as maltose or particularly cellobiose, and others comprise N-acyl amido derivatives of aminoacids, di- or tri-carboxylic acids or cyclohexane. The present invention is directed particularly to compositions in which a continuous phase comprising a water-immiscible oil is solidified with one or more N-acyl amido derivatives of aminoacids.

Many N-acyl amido derivatives of aminoacids that are suitable for solidifying cosmetically-acceptable oils to a greater or lesser extent have been described by Ajinomoto Co Ltd in U.S. Pat. No. 3,969,087, including in particular derivatives of glutamic acid or aspartic acid. The derivative disclosed therein that was apparently the most preferred by Ajinomoto was N-lauroylglutamic acid, -di-n-butylamide, as also indicated by the fact that for many years, it was the only such material that was commercially available from them (trade name GP-1).

GP-1 structurant has been disclosed for use or used in structuring water-immiscible oils in cosmetic sticks, but often not by itself and instead in combination with one or more structurants, for example providing the minor weight proportion of the structurant mixture. Thus, for example Hofrichter et al (Procter & Gamble) in U.S. Pat. No. 5,650,144, U.S. Pat. No. 5,591,424 and U.S. Pat. No. 5,429,816 describe the formation of sticks in which a cosmetic oil is solidified with a mixture of a major proportion of 12-hydroxystearic acid or related compounds (primary gellant) and a minor proportion of an N-acyl aminoacid amide (secondary gellant), exemplifying GP-1 and related N-acyl glutamic acid di-amides in a weight proportion to 12-HSA of 2:6. The combination of hydroxystearic acid and N-acyl aminoacid amides gellants described in the Hofrichter patents supra can be processed under acceptable processing conditions, which is a very desirable attribute. However, the combination of the N-acyl aminoacid amides with hydroxy-stearic acid as primary structurant has a second consequence. Such combinations when made prior to this invention were opaque, rather than translucent.

In the course of investigations leading to the instant invention, it was found that although sticks can indeed be made using N-acyl aminoacid amides like GP-1 as gellant, the resultant product was comparatively soft when made, depositing a "wet" oily film on skin when applied topically. Such a feel is disliked by consumers. Such disadvantageous properties tended to become worse during storage of the product.

The comparative softness of such products has been recognised by Ajinomoto themselves. More recently, in USA-2002/0159961, Ajinomoto has described a selection of N-acyl amido derivatives of aminoacids from within the overall ranges described in U.S. Pat. No. 3,969,087. In this selection, the alkyl group $R^3$ in the N-acyl substituent —CO—$R^3$ is characterised by containing from 7 to 10 carbon atoms, and may be branched. The '961 specification discloses that the new selection of aminoacid derivatives can be employed to gel non-polar organic liquids to produce harder gels. The '961 specification also discloses the formation of antiperspirant compositions gelled by a representative member of their selection or mixed with GP-1, but once again their selected gellant in which the acyl N-substituent is branched is employed as the minor gellant in combination with hydroxystearic acid as primary gellant (weight ratio of 2:7). Such products are again opaque.

One of the problems faced in the course of devising the instant invention is that of the temperature at which a water-immiscible cosmetic oil gels when employing N-acyl aminoacid amide gellant having a branched N-acyl substituent compared with the same amount of a like gellant having a linear N-acyl substituent. For otherwise identical compositions, the gellant having the branched N-acyl substituent gels such a composition at a significantly higher temperature, for example a difference of over 20° C. A mixture of a gellant such as an N-acyl aminoacid amide and a carrier oil needs to be heated to substantially above its gelation temperature before the gellant dissolves, and it is commonly impractical for antiperspirant or deodorant compositions to be heated to amide dissolution temperatures, so that, in practice, it is impractical to redissolve the gellant by heating such a composition once it has gelled and it accordingly remains gelled. Consequently, it is inherently disadvantageous to employ a gellant that gels the composition at a significantly higher temperature, such as to above the boiling point of water. An elevated gelation temperature introduces a substantial risk that the composition would be gelled before it has been cooled to a temperature at which an active constituent or a temperature sensitive constituent can be introduced, or that the very act of introduction of the active constituting a significant proportion of the overall composition would lower the composition temperature rapidly below the oil gelation temperature, rendering subsequent operations extremely difficult if not impossible on a bulk scale, such as filling of product dispensers.

There is further potentially serious complication in the context of seeking to make a translucent composition. If the temperature of the mixture containing a suspended antiperspirant active is taken above 100° C., there is an increased risk of water evaporating off from the antiperspirant. This has the effect of inevitably altering the refractive index of the particulate solid. The very nature of the process means that it is not readily controlled and the extent of loss is not easily predicted. Translucent compositions containing commonly available particulate substances are, in practice, often obtained by refractive index matching of carrier and suspended material. Hence, if the formulation is prepared under conditions at which water evaporates off, refractive index matching becomes a matter of chance rather than control. Also the risk is increased that different antiperspirant particles lose water to a differing extent, increasing the refractive index spread of the suspended material, and thereby inevitably meaning that at least some suspended particles will not be refractive index matched causing opaqueness.

SUMMARY OF THE INVENTION

It is an object of the present invention to avoid or at least ameliorate one or more of the difficulties or disadvantages indicated hereinabove in the preparation of solidified water-immiscible oils containing a cosmetic active ingredient.

According to one aspect of the present invention, there is provided a cosmetic antiperspirant or deodorant composition as described hereinafter in claim 1.

By the employment of the combination of fibre-forming structurants described herein, it is possible to prepare translucent cosmetic sticks in a manner that ameliorates one or more of the problems identified hereinbefore.

By translucent herein is meant that the composition has at least 0.2%, preferably at least 0.3% light transmittance at 580 nm through a 1 cm thickness of the composition at 22° C., and more preferably, at least 1%.

The invention compositions herein are anhydrous, by which is meant herein that the liquid carrier oils do not contain a polar phase such as a dispersed aqueous phase.

According to a second aspect of the present invention, there is provided a process for the preparation of an cosmetic antiperspirant or deodorant composition as described in claim 50.

According to a third aspect of the present invention there is provided a cosmetic method for inhibiting or controlling perspiration and/or body malodours by the topical application to skin of an effective amount of a composition according to the first aspect.

DETAILED DESCRIPTION OF THE INVENTION AND PREFERRED EMBODIMENTS THEREOF

The present invention relates to antiperspirant or deodorant sticks containing a cosmetic antiperspirant or deodorant active ingredient in which the water-immiscible oil phase is solidified using a mixture of at least two classes of fibre-forming structurants containing an amido linkage of which one class is gellant (i) an N-acyl aminoacid amide, the acyl group containing a branched alkyl group of 4 to 12 carbon atoms. Herein, it is considered that cyclic dipeptides contain an amido linkage.

Gellant (i)

Gellant (i) is an N-acyl aminoacid amide that satisfies general formula (1) $A^X$—CO—$R^X$ in which $A^X$ represents the residue of an amino acid amide and $R^X$ represents a branched alkyl group containing from 4 to 12 carbon atoms and sometimes 7 to 10 carbon atoms. In many instances, the aminoacid amide residue $A^X$ can be represented by formula (2)

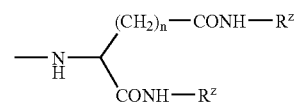

in which n represents an integer of 1 or 2 and $R^Z$ represents an alkyl group, which can be linear or branched, containing from 1 to 10 and particularly from 3 to 5 carbon atoms, each of which $R^Z$ groups can be the same or different. Accordingly, the amino acid from which such an amide residue $A^X$ is derivable is glutamic or aspartic acid. In some especially preferred embodiments, each $R^Z$ represents a butyl group, especially an n-butyl group, and particularly in the derivative of glutamic acid, which residue is represented by formula (3)

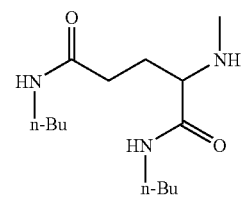

In formula (1), $R^X$ preferably represents an alkyl group containing either one or two or possibly three side chains, such as particularly one side chain. Desirably, any side chain in $R^X$ contains from 1 to 4 carbon atoms, such as methyl, ethyl propyl or butyl, and often from 1 to 3 carbon atoms, of which ethyl is very convenient. The alkyl backbone preferably contains from 4 to 8 carbon atoms and often from 4 to 7 carbon atoms, or particularly 7 or 8 carbon atoms. The location of the side chain along the alkyl group backbone is at the discretion of the producer, of which the 2 position is often favoured. An especially desirable branched chain group for $R^X$ is 1-ethylpentyl, so that the resultant acyl group is 2-ethylhexanoyl. Other branched chain groups for $R^X$ include 1-methylbutyl, isobutyl and 1-butylheptyl. It is particularly desirable to employ a gellant (i) in which $R^X$ is according to one or more of the branched alkyl groups named above and the amide residue is derived from glutamic acid dibutylamide.

The weight proportion of gellant (i) in the composition is commonly selected in the range of 0.75 to 8%, often at least 1%, in many desirable embodiments is at least 1.5% w/w and particularly at least 2% w/w. It is often unnecessary to employ more than 6% w/w of gellant (i) in the composition. The proportion of gellant in the composition can also be determined by relation to the water-immiscible phase which it is structuring. The weight proportion of gellant (i) is usually selected in the range of from 1 to 15% w/w of the water-immiscible phase, commonly at least 2%, and is often present in a proportion of at least 3% w/w of that phase. Its weight proportion of that phase in a number of preferred embodiments is up to 11%. The weight proportion of each gellant in the composition or water-immiscible phase will often be selected in concert with the choice of co-gellant or gellants, the weight of co-gellant or gellants and the desired hardness of the stick.

Gellant (i) is employed in conjunction with a second amide-fibre-forming structurant, gellant (ii). Within such second amide fibre-forming structurants are included gellant (iia) N-acyl aminoacid amides other than the branched-chain substituted N-acyl aminoacid amides of gellant (i), gellant (iib) cyclodipeptides, and gellant (iic) 1,2-diamido substituted cyclohexane. One or more of gellants (iia) to (iic) can be employed simultaneously.

N-acyl aminoacid amides according to gellant (iia) are described in U.S. Pat. No. 3,969,087. A list of many of such amides and the general method of manufacture are described in said patent specification in column 1 line 63 to column 4 line 47, and specific amido derivatives are named in Example 1 in column 6 to 8, which passages from the text are incorporated herein by reference. Herein, gellant (iia) often satisfies formula (4) $A^y$—CO—$R^Y$ in which $A^Y$ represents an amino acid amide residue and $R^Y$ represents a linear alkyl group containing from 9 to 21 carbon atoms. Highly desirably, $A^Y$ represents an amino acid amide in accordance with the formula (5)

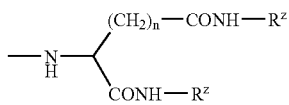

in which n represents an integer of 1 or 2 and $R^Z$ represents an alkyl group, which can be linear or branched, containing from 1 to 10 and particularly from 3 to 5 carbon atoms, each of which $R^Z$ groups can be the same or different. Accordingly, the amino acid from which such an amide residue $A^Y$ is derivable is glutamic or aspartic acid. In some especially preferred embodiments, each $R^Z$ represents a butyl group, especially an n-butyl group, and particularly is the derivative of glutamic acid. This is likewise represented by formula (3) given supra for residue $A^X$.

In formula (4), $R^Y$ often contains from 9 to 15 linear carbons, of which one preferred group comprises undecyl. N-Lauroyl-L-glutamic acid di-n-butylamide, formula (6)

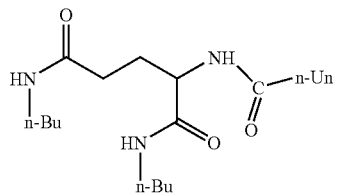

(n-Un=undecyl) employed in Example 14 of '087, is an especially desirable amide structurant for employment in the instant invention compositions and is commercially available from Ajinomoto under their trade designation GP-1.

Herein, the weight proportion of gellant (iia) in the composition is commonly selected in the range of 1 to 8% and in many desirable embodiments is at least 1.5% w/w and particularly at lest 2% w/w. It is often unnecessary to employ more than 6% w/w of gellant (i) in the composition. The proportion of gellant in the composition can also be determined by relation to the water-immiscible phase which it is structuring. The weight proportion of gellant (iia) is usually selected in the range of from 1.5 to 12% w/w of the water-immiscible phase and is often present in a proportion of at least 2% or 2.5% w/w of that phase. Its weight proportion of that phase in a number of preferred embodiments is up to 8%. The weight proportion of the gellant in the composition or water-immiscible phase will often be selected in concert with the choice of co-gellant or gellants, the weight of co-gellant or gellants and the desired hardness of the stick.

The weight ratio of gellant (i) to gellant (iia) is often selected in the range of from 4.5:1 to 1:4.5 and commonly from 3:1 to 1:3. In many instance the weight ratio is no higher than 2:1 and in such or other instances, the weight ratio is at least 1:2. A convenient weight ratio can be in the range of 1.1:1 to 1:1.1.

The combined weight proportion of gellants (i) and (iia) in the composition is often selected in the range of from 4 to 10% and in some well desired embodiments from 5 to 8%. When expressed in terms of the weight proportion of the two gellants in the water-immiscible phase, this is often from 6 to 15% w/w of the phase and in many desirable embodiments from 7.5 to 12% w/w.

A second class of amide gellants (iib) suitable for employment in the instant invention comprises structurants which satisfy the following general formula:

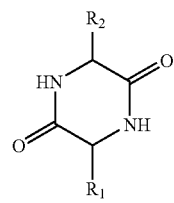

in which one of $R_1$ and $R_2$ represents an alkyl, alkyl ester group and the other represents an alkyl or alkaryl group. Examples of such amides are described in two papers by Hanabusa et al, entitled respectively Cyclo(dipeptide)s as low molecular-mass Gelling Agents to harden Organic Fluids, J. Chem Soc. Commun., 1994 pp1401/2, and Low Molecular Weight Gelators for Organic Fluids: Gelation using a Family of Cyclo(dipeptide)s, in the Journal of Colloid and Interface Science 224, 231-244 (2000), which descriptions of amide structurants are incorporated herein by reference.

However, it is especially preferred to employ herein a sub-class of cyclodipeptides not expressly disclosed by Hanabusa, which sub-class satisfies the general formula:

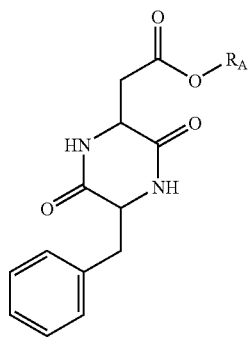

in which $R_A$ represents a carbocyclic or heterocyclic group containing not more than 2 rings. Such materials are sometimes herein referred to as DOPA derivatives.

In DOPA derivatives, $R_A$ can comprise two fused rings, but preferably comprises a single six membered ring, either carbocyclic or heterocyclic, or a bridged ring. When A is carbocyclic, it can be either saturated or unsaturated, preferably unsaturated or aromatic. When $R_A$ is heterocyclic, it is preferably saturated.

Although the cyclic group within $R_A$ can be unsubstituted, it is preferably substituted by at least one alkyl substituent, which preferably contains no more that 16 carbon atoms. In some highly desirable embodiments the alkyl substituent has a longest chain length of up to 4 carbon atoms, and in certain of those a total carbon content of up to 5 carbon atoms. The alkyl substituent may be linear or branched. Preferred examples include methyl, ethyl, propyl, isopropyl, butyl isobutyl or t-butyl or isopentyl. In a number of very suitable DOPA derivatives, $R_A$ contains two or more alkyl substituents and especially those selected from the above list of preferred examples. The alkyl substituents may be the same, such as two or more methyl substituents, or may be a combination of different substituents such as a methyl and isopropyl substituents. When $R_A$ is saturated, the substituents may depend from the same carbon atom in the ring, such as two methyl groups, or from different carbon atoms. In several highly desirable derivatives, two alkyl substituents are meta or para to each other, for example meta methyl groups or a para methyl and isopropyl group. In yet other derivatives, the ring may include a methylene bridge, which preferably likewise completes a six-membered ring.

In some suitable DOPA derivatives, the or one alkyl substituent may be ortho or para to the bond with the DOPA residue, as in 4-methyl-phenyl-. In some or other DOPA derivatives, the bond with the DOPA residue is meta to one or preferably two methyl substituents.

When $R_A$ is heterocyclic, the heterocyclic atom is suitably nitrogen. Conveniently, the heterocyclic atom can be para to the bond with the DOPA residue. Moreover, in a number of desirable derivatives, the heteroatom is ortho to at least one alkyl group, better in a saturated ring and especially to up to 4 ortho methyl groups.

The group $R_A$ is often most easily referred to as the residue from the corresponding alcohol which may be reacted with DOPA to form the ester linkage. Thus, desirable examples of $R_A$ include the residues from 4-alkyl phenol, such as 4-nonyl-phenol, and 2,6-dialkyl- or 2,2,6,6-tetraalkyl-4-piperidinol, such as 2,2,6,6-tetramethyl-4-piperidinol.

In some preferred DOPA derivatives, the ring in $R_A$ is carbocyclic, and is substituted by at least two alkyl groups of which at least one is methyl and the other or one of the others is isopropyl. Examples of such preferred $R_A$ residues include menthol, isopinocamphenol and 3,5-dialkyl cyclohexanol such as 3,5-dimethyl cyclohexanol. Especially preferred $R_A$ residues include thymol. Yet others include the DOPA derivatives from carveol and carvacrol.

The DOPA derivatives used in this invention may be a mixture of compounds within the general formulae given, or may be a single compound.

The DOPA derivatives can be prepared by reacting the respective alcohol with DOPA in acid form (DOPAA), or possibly with an acid chloride, or possibly an anhydride or an ester containing a DOPA residue. DOPAA can be obtained by cyclising aspartame. DOPAA can be reacted with the relevant alcohol of formula $R_AOH$, preferably in a mole ratio to the DOPAA of at least 2:1 in dimethyl sulphoxide, in a ratio of from 6:1 to 12:1, in the presence of a promoter, such as a carbonyldiimidazole, in an amount preferably from 0.5 to 2 moles of promoter per mole of DOPA acid. The reaction is conveniently carried out at a temperature from 40 to 60° C.

The weight proportion of gellant (iib) in the composition is commonly selected in the range of 0.4 to 4% and in many desirable embodiments is at least 0.6% w/w. It is often unnecessary to employ more than 3% w/w of gellant (iib) in the composition and convenient to employ up to 2% or 2.5% w/w. The proportion of gellant in the composition can also be determined by relation to the water-immiscible oils which it is structuring. The weight proportion of gellant (iib) is usually selected in the range of from 0.6 to 6% w/w of the water-immiscible oils and is often present in a proportion of at least 1% w/w of those oils. Its weight proportion in those oils in a number of preferred embodiments is up to 3.75%. In some highly desirable embodiments, its weight proportion in the oils is from 1.2 to 2.5% w/w.

The weight ratio of gellant (i) to gellant (iib) is often selected in the range of from 1:1 to 5:1. In many instances the weight ratio is no higher than 4:1 and commonly up to 3:1. In such or other instances, the weight ratio is advantageously at least 1.5:1. A convenient weight ratio can be in the range of 1.5:1 to 2.5:1.

The combined weight proportion of gellants (i) and (iib) in the composition is often selected in the range of from 1.5 to 10% and in some well desired embodiments from 2 to 6% and a particularly desirable range therein is up to 5% w/w. When expressed in terms of the weight proportion of the two gellants in the water-immiscible oils, this is often from 2 to 12% w/w of the oils, in many desirable embodiments from 3 to 8% w/w, and particularly from 3.5 to 6% w/w.

A third class of amido-substituted fibre-forming structurants, (iic) comprises 1,2-di-amido-substituted cyclohexane, and particularly such compounds in which each amido substituent accords with the general formula (7)—$(CH_2)_v$—NH—CO—$R^{111}$) in which $R^{111}$ represents an alkyl group of from 5 to 27 carbon atoms and v is an integer selected from zero and one, and preferably v is zero. $R^{111}$ can be linear or branched. Preferably the number of carbons in $R^{111}$ is selected in the range of 8 to 20. For example undecyl, dodecyl, 2-ethylhexyl, octadecyl, or dimethyloctyl.

Herein, the weight proportion of gellant (iic) in the composition is commonly selected in the range of 1 to 8% and in many desirable embodiments is at least 1.5% w/w and particularly at least 2% w/w. It is often unnecessary to employ more than 6% w/w of gellant (i) in the composition. The proportion of gellant in the composition can also be determined by relation to the water-immiscible oils which it is structuring. The weight proportion of gellant (iic) is usually selected in the range of from 1.5 to 12% w/w of the water-immiscible oils and is often present in a proportion of at least 2 or 2.5% w/w of those oils. Its weight proportion of those oils in a number of preferred embodiments is up to 8%. The weight proportion of the gellant in the composition or water-immiscible oils will often be selected in concert with the choice of co-gellant or gellants, the weight of co-gellant or gellants and the desired hardness of the stick.

The weight ratio of gellant (i) to gellant (iic) is often selected in the range of from 3:1 to 1:3. In many instance the weight ratio is no higher than 2:1 and in such or other instances, the weight ratio is at least 1:2. A convenient weight ratio can be in the range of 1.1:1 to 1:1.1.

The combined weight proportion of gellants (i) and (iic) in the composition is often selected in the range of from 4 to 10% and in some well desired embodiments from 5 to 8%.

When expressed in terms of the weight proportion of the two gellants in the water-immiscible oils, this is often from 6 to 15% w/w of the oils and in many desirable embodiments from 7.5 to 12% w/w.

The gellants disclosed herein are selected by virtue of their capability to form stick compositions, for example in a conventional stick making process or an advantageous modification thereto, having the desirable combination of properties both as regards a translucent or transparent appearance as well as desirable skin-feel (sensory) attributes. Some amido gellant combinations investigated during the course of the instant invention generated opaque sticks, some are not susceptible to conventional stick processing and some amido-gellants produce sticks with poor or very poor sensory attributes.

Carrier Oils

The water-immiscible carrier liquid for the continuos phase comprises one or a mixture of materials which are relatively hydrophobic so as to be immiscible in water. Following partition between the continuous phase and the disperse phase, a small fraction of hydrophilic liquid may remain in the continuous phase, provided the overall carrier liquid mixture is immiscible with water. It will generally be desired that the carrier oils mixture is liquid (in the absence of structurant) at temperatures of 15° C. and above. It may have some volatility but its vapour pressure will generally be less than 4 kPa (30 mmHg) at 25° C. so that the material can be referred to as an oil or mixture of oils. More specifically, it is desirable that at least 80% by weight of the hydrophobic carrier liquid should consist of materials with a vapour pressure not over this value of 4 kPa at 25° C.

It is preferred that the hydrophobic carrier material includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa to 2 kPa at 25° C.

It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ m$^2$/sec (10 centistokes), and particularly above $10^{-7}$ m$^2$/sec (0.1 centistokes), the linear siloxanes normally exhibiting a viscosity of below $5 \times 10^{-6}$ m$^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic carrier employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include products available under the trademarks Dow Corning 556 and Dow Corning 200 series. Other non volatile silicone oils include that bearing the trademark DC704. Incorporation of at least some non-volatile silicone oil having a high refractive index such as of above 1.5, e.g. at least 10% by weight (preferably at least 25% to 100% and particularly from 40 to 80%) of the silicone oils is often beneficial in some compositions, because this renders it easier to match the refractive index of the constituents of the composition and thereby easier to produce transparent or translucent formulations.

The water-immiscible liquid carrier may contain from 0% to 100% by weight of one or more liquid silicones. Preferably, there is sufficient liquid silicone to provide at least 10%, better at least 15%, by weight of the whole composition.

Silicon-free hydrophobic liquids can be used instead of, or more preferably in addition to liquid silicones. Silicon-free hydrophobic organic liquids which can be incorporated include liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms.

Other suitable hydrophobic carriers comprise liquid aliphatic or aromatic esters. Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable liquid aromatic esters, preferably having a melting point of below 20° C., include fatty alkyl benzoates. Examples of such esters include suitable $C_8$ to $C_{18}$ alkyl benzoates or mixtures thereof, including in particular $C_{12}$ to $C_{15}$ alkyl benzoates e.g. those available under the trademark Finsolv. An aryl benzoate, such as benzyl benzoate can also be used. Incorporation of such alkyl or aryl benzoate esters as at least a fraction of the hydrophobic carrier liquid can be advantageous, because they can widen the window of carriers for obtaining translucent or transparent formulations.

Further instances of suitable hydrophobic carriers comprise liquid aliphatic ethers derived from at least one fatty alcohol, such as myristyl ether derivatives e.g. PPG-3 myristyl ether or lower alkyl ethers of polygylcols such as an ether having named as PPG-14 butyl ether by the CTFA.

Aliphatic alcohols which are liquid at 20° C. may be employed herein, and it is especially desirable to employ those which are water-immiscible, and particular those having a boiling point of higher than 100° C. These include branched chain alcohols of at least 10 carbon atoms and in many instances up to 30 carbon atoms, particularly 15 to 25, such as isostearyl alcohol, hexyl-decanol octyl-dodecanol and decyl-decanol. Other suitable water-immiscible alcohols include intermediate chain length linear alcohols, commonly containing from 9 to 13 carbon atoms, such as decanol or dodecanol. A further suitable alcohol is benzyl alcohol. Such alcohols can assist in the process of forming a solution of the amido-substituted gellants (i) and/or (iia) to (iic) in a water-immiscible carrier liquid during the manufacture of structured gels. Such alcohols can often constitute from at least 10% or 15% by weight of the water-immiscible liquid carrier mixture, in many desirable mixtures comprising up to 70% or 80% of the mixture. In a number of convenient formulations, the proportion of such aliphatic alcohols in said mixture is from 10 or 15% to 30% by weight and in some others, the proportion is greater than 30% by weight.

However, aliphatic alcohols which are solid at 20° C., normally linear alcohols, such as stearyl alcohol are preferably absent or present in no more than 3% by weight of the whole composition, as indicated hereinbefore, since they lead to visible white deposits when a composition is topically applied to skin.

Silicon-free liquids can constitute from 0-100% of the water-immiscible liquid carrier, but it is preferred that some silicone oil is present and that the amount of silicon-free constituents preferably constitutes up to 50 or 60% or even up to 80% of water-immiscible carrier liquid and in many instances from 10 to 60% by weight, e.g. 15 to 30% or 30 to 60% by weight, of the carrier liquid.

It will be recognised that the proportions of the oil constituents are selected so as to achieve refractive index (sometimes abbreviated herein to RI) matching with the suspended particulate antiperspirant or deodorant active. This tempers the disclosures made previously herein with respect to proportions of oil constituents that are employable. In practice a mixture of oils will normally be employed, unless a single oil has an RI which matches that of the suspended particulate active. The choice of oils will be made in conjunction with the choice of suspended active. The choice of oils can be made within the same class of oils where those oils can combine to generate a suitable RI (obtained by a weight average of the RIs of constituent oils) or by combination of oils from two or more classes of oils. Thus, by way of example, a cyclomethicone silicone oil having an RI of just below 1.40 can be combined in a suitable proportion with a linear alkylaryl-substituted silicone oil with an RI in the region of 1.54 to 1.56 to attain a matching RI to that of an aluminium chlorohydrate antiperspirant salt having for example about 1.51. Likewise a fraction of the oil can comprise a branched aliphatic alcohol or benzyl alcohol, for example replacing some or all of the cyclomethicone oil.

The Refractive Index employed herein for an oil is that listed or measured at 22° C., unless otherwise expressly indicated. Data-sheets for commercially available cosmetic oils commonly include the refractive index, and where not included, it can be measured conveniently using commercially available refractometers, such as an RFM 340™ Refractometer available from Bellingham and Stanley Ltd. Refractive index matching is made herein at or for 22° C. unless otherwise expressly stated.

The compositions herein may contain a more polar liquid, but only to the extent that it is miscible with the water-immiscible oil/mixture. In many instances this limits the proportion of such a constituent to no more than 15% w/w of the combined liquids, and in many instances to not more than 10% w/w on the same basis, though of course the proportion will inevitably vary from one polar liquid to another. One class of material which is worthy of mention is that of low molecular weight polyhydric alcohols and oligomers thereof, commonly up to a molecular weight of about 150. This class desirably contains two hydroxyl substituents, as in ethylene glycol, propylene glycol, dipropylene glycol or a dihydroxyhexane or three hydroxy substituent as in glycerol. Glycerol and 1,6-dihydroxyhexane are more favoured.

Antiperspirant or Deodorant Actives

Antiperspirant Active

The composition preferably contains an antiperspirant active. Antiperspirant actives, are preferably incorporated in an amount of from 0.5-50%, particularly from 5 to 30% or 40% and especially from 5 or 10% to 30% of the weight of the composition. It is often considered that the main benefit from incorporating of up to 5% of an antiperspirant active in a stick composition is manifest in reducing body odour, and that as the proportion of antiperspirant active increases, so the efficacy of that composition at controlling perspiration increases.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates.

Aluminium halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever N V et al), the contents of which specification is incorporated herein by reference. Such activated aluminium chlorohydrates are made by a method in which the weight concentration of aluminium compounds in the solution is controlled within specified limits and simultaneously the temperature of that solution is controlled within a specified elevated temperature range whilst polymeric aluminium species are formed, and drying conditions are strictly controlled as described in the said EP-A-6739. Some activated salts do not retain their enhanced activity in the presence of water but are useful in substantially anhydrous formulations, i.e. formulations that do not contain a distinct aqueous phase.

Zirconium actives can usually be represented by the empirical general formula: $ZrO(OH)_{2n-nz}B_z.wH_2O$ in which z is a variable in the range of from 0.9 to 2.0 so that the value 2n−nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have co-ordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis, though with differing particle size distributions. Consequently, such actives would become suitable for employment in the instant invention if their production has been suitably adapted to meet the invention particle size criteria.

The proportion of solid antiperspirant salt in a suspension composition normally includes the weight of any water of hydration and any complexing agent that may also be present in the solid active.

The particulate antiperspirant employed in the instant invention has a refractive index (RI) of at least 1.49 and not higher than 1.57. Actives which are free from zirconium tend to have an RI of from 1.49 to 1.54, depending on their formula and at least partly on their residual water content. Likewise, actives which contain zirconium tend to have an RI of from 1.52 to 1.57. The water content of the antiperspirant active can be modified by hydration after dried active has been made or by drying to an intermediate water content. The actives can also be treated with a small amount of an alcohol such a C2 to C4 aliphatic alcohol, e.g. ethanol, to alter its RI.

The RI of particulate material, viz the antiperspirant salt can be measured by a conventional Becke line method in which particles of the solid are suspended in a range of oil drops, each of different, but known RI, and the suspension is viewed through a microscope. The particle has a coloured fringe that moves into the oil phase or towards its centre as the focus of the instrument is slightly altered, the direction depending on which has the higher RI.

Herein, the RIs of the antiperspirant active and the suspended antiperspirant active are matched to within 0.02. Herein, RIs and differences between them are those at 22° C. unless otherwise specified. Preferably, the difference between the refractive indices is less than 0.01 and especially less than 0.005. This can be achieved by varying the proportions of liquids constituting the carrier, its resultant RI being a weight averaged RIs of the carrier constituents and/or by varying the RI of the antiperspirant active as indicated above. Under many circumstances, RI matching of the constituents of the invention formulations is not absolutely perfect. Small variations can arise in practice, for example from changes in temperature or between different batches of ingredients. Thus, such RI difference in the invention compositions herein on the shelf or in the home is often at least 0.0005, and sometimes at least 0.001. Advantageously, by selecting the particulate antiperspirant active in accordance with the criteria described herein, and particularly with increasingly preferred criteria, the benefit of clear formulations can be retained even when the abovementioned RIs do not match exactly.

The antiperspirant active employed herein comprises small particles, of which not more than 50% by weight have a diameter of below 10 µm. Preferably less than 40% of particles by weight have a particle size of below 10 µm. In practice, desirable antiperspirant actives contain at least 1% and often at least 5% by weight of particles in the range of from 1 to below 10 µM. In general, at least 90% by weight of the antiperspirant active has a particle size of below 100 µm, in many instances at least 95% by weight and in some preferred compositions at least 99% by weight below 100 µM. In many embodiments herein, the active has a weight average particle size of from 12 to 50 µm. It will be recognised, though that materials having such an average particle size are suitable only if they also meet the criterion given above about maximum proportion of particles below 10 µm.

The fineness, coarseness and particle size distribution of antiperspirant actives that are produced can vary substantially, depending on their manner and conditions of manufacture, including the type of drying stage employed, and any subsequent processing stages, such as milling, and/or classification. Actives having an appropriate particle size distribution to satisfy the above selection criterion can be made by suitably controlling conventional drying and milling techniques in manners known to persons skilled in the art of making antiperspirant actives, so as to reduce the proportion of particles produced of sub 10 µm diameter. Methods can include control of droplet size in spray drying. Where a product is produced, for example by spray drying or freeze drying that has excessive proportion of sub 10 µm diameter particles, the proportion can be lowered by conventional classification apparatus.

Furthermore, it is highly desirable to employ antiperspirant active material which is free or substantially free from hollow particles. In this context, substantially free indicates a content of less than 10% by weight hollow spheres, and preferably less than 5% by weight. Some drying techniques, e.g. spray drying, can produce materials which contain greater than such a proportion of hollow spheres. The proportion of hollow spheres in an antiperspirant material can be reduced by milling the particulate material, such as by ball or swing milling.

Deodorant Actives

Suitable deodorant actives can comprise deodorant effective concentrations of antiperspirant metal salts, deoperfumes, and/or microbicides, including particularly bactericides, such as chlorinated aromatics, including biguanide derivatives, of which materials known as Igasan DP300™ (triclosan), Tricloban™, and Chlorhexidine warrant specific mention. A yet another class comprises biguanide salts such as are available under the trade mark Cosmocil™. Deodorant actives are commonly employed at a concentration of from 0.1 to 25% by weight.

Optional Ingredients

Optional ingredients include wash-off agents, often present in an amount of up to 10% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

The compositions herein can incorporate one or more cosmetic adjuncts conventionally contemplatable for cosmetic solids or soft solids a moisturiser such as glycerol, for example in an amount of up to about 5%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

It will be recognised that where any adjunct is incorporated into the liquid oil phase, it will often tend to affect the RI of the resultant mixture. Accordingly, its presence is to be taken into account when determining the final RI of the mixture, for example by measuring a sample of it.

In order to achieve good light transmission through a composition, the refractive index of the water-immiscible oil phase and the refractive index of the suspended particulate material should match within 0.003 units preferably 0.002 units.

Suspension sticks made with the combination of gellants, (i) and one or more of (iia) to (iid), are non-whitening and have a good skin feel. They can also be made with sufficient translucency to be perceived as clear.

Composition Preparation

A convenient process sequence for preparing a composition according to the present invention comprises first forming a solution of the structurant combination in the water-immiscible liquid or one of the water-immiscible liquids. This is normally carried out by agitating the mixture at a temperature sufficiently high that all the structurants dissolve (the dissolution temperature) such as a temperature in a range from 70 to 140° C. Any oil-soluble cosmetic adjunct can be introduced into oil phase, either before or after the introduction of the structurants. Commonly the resultant structurant solution is allowed to cool to a temperature that is intermediate between that at which the structurants dissolved and the temperature at which it would set, often reaching a temperature in the region of 60 to 90° C.

The preparative route commonly includes the steps of identifying the refractive indexes of the suspended particulate material and the oil carrier phase in which is suspended and matching the refractive indexes by selecting ratios of the oil constituents to form a mixture having an RI that matches the suspended particulate material and/or treating the suspended material for example by hydration or dehydration until it matches the carrier oils refractive index.

In some convenient preparative routes, it is desirable to dissolve all or a fraction of the amide-substituted structurants in a first fraction of the composition, such as an alcohol, e.g. an alcoholic carrier fluid, i.e., a branched aliphatic alcohol, e.g. isostearyl alcohol or octyldodecanol, optionally in conjunction with an alcohol having some water-miscibility and boiling point above the dissolution temperature of DOPAD in the alcoholic fluid. This enables the remainder of the carrier fluids to avoid being heated to the temperature at which the structurants dissolve or melt. The proportion of the carrier fluids for dissolving the structurants is often from 15 to 65% by weight of the carrier fluids, and particularly from 20 to 40%.

Preferably the particulate material is introduced into a second fraction of the carrier oils, for example silicone and/or ester and/or hydrocarbon oils and thereafter, and thereafter the first fraction containing dissolved structurant and second fraction containing suspended particulate material are mixed at a temperature above that at which the composition gels, and often from 5° C. to 30° C. above the regular setting temperature of the composition, dispensing containers are filled and cooled or allowed to cool to ambient temperature. Cooling may be brought about by nothing more than allowing the container and contents to cool. Cooling may be assisted by blowing ambient or even refrigerated air over the containers and their contents.

Product Dispenser

Suspension sticks according to the present invention are normally housed in dispensing containers, the shape and size of which, the materials of their construction and the mechanisms employed therein for dispensing the antiperspirant sticks are those commensurate with the cosmetic. An antiperspirant or deodorant stick is often housed in a barrel, commonly of circular or elliptical transverse cross section, having an open end through which the stick can pass and an opposed closed end, commonly comprising a platform or elevator that is axially moveable along the barrel. The platform can be raised by the insertion of a finger or more commonly by rotation of an externally exposed rotor wheel that rotates a threaded spindle extending axially through a co-operating threaded bore in the platform. The barrel normally also has a removable cap that can fit over its open end. The barrel is normally made from an extrudable thermoplastic such as polypropylene or polyethylene.

The present invention also provides translucent cosmetic antiperspirant or deodorant products comprising an invention cosmetic stick as described hereinbefore disposed within a dispensing barrel.

Having summarised compositions according to the present invention and described preferred embodiments, specific embodiments thereof will now be described in more detail by way of example only.

The following constituents were employed in exemplified and comparison suspension sticks hereinafter.

| Ref | CTFA or IUPAC name | Trade name and/or supplier | Refractive Index |
|---|---|---|---|
| C1 | Methylphenyl-trisiloxane | DC704, Dow Corning | 1.556 |
| C2 | Methylaryldi-siloxane | Sample oil, Dow Corning | 1.558 |
| C3 | 2-hexyl-decanol | Eutanol G16, Cognis | 1.448 |
| C4 | Isostearyl alcohol | Prisorine 3515, Uniqema | 1.456 |
| C5 | Dipropylene glycol dibenzoate | Finsolv PG22 Finetex | 1.5222 |
| C6 | Methyl phenyl siloxane | KF 56: Shin-Etsu | 1.5040 |
| C7 | Diethylhexyl 2,6-naphthalate | Hallbrite TQ, C P Hall | 1.5324 |
| G1 | N-(2-ethyl hexanoyl)-L-glutamic acid di-n-butylamide | GA-01, Ajinomoto | |
| G2 | N-lauroyl-L-glutamic acid di-n-butylamide | GP-1, Ajinomoto | |
| G3 | (5-benzyl-3,6-dioxo-2-piperazin-2-yl)-acetic acid, 2-isopropyl-5-methyl-phenyl ester | preparation as per Ex 1.2 of PCT/EP 02/14525 (published as WO 03/059307) | |
| G4 | N N'-bis (dodecanoyl)-1,2-diaminocyclohexane (non optically active cis/trans mixture) | Preparation as in U.S. Pat. No. 6410003 | |
| G5 | N N'-bis (2-ethylhexanoyl)-1,2-diaminocyclohexane (non optically active cis/trans mixture). | Preparation as in U.S. Pat. No. 6410003 | |
| G6 | isopentanoyl-L-glutamic acid di-n-butylamide | Preparation hereinbelow | |
| G7 | 2-butyl octanoyl-L-glutamic acid di-n-butylamide | Preparation hereinbelow | |
| S1 | Activated Aluminium chlorohydrate | A418, Summit | 1.530 |
| S2 | Al/Zr pentachloro-hydrex glycine complex, 25% wt/wt <10 µm, few hollow particles | sample P5G B K Giulini | 1.534 |
| S3 | Activated Al/Zr pentachloro-hydrex glycine complex, 15% wt/wt <10 µm, few hollow particles | sample P5G-LR B K Giulini | 1.531 |
| S4 | Hydrophobic Silica | HDK H30 - Wacker Chemie | |
| F | Fragrance | | |

Measurements of payoff of the stick and visible deposits (whiteness) in the Examples and Comparisons were made on black cotton, 24 hours after application of the stick.

EXAMPLES 1.1 TO 1.4 AND COMPARISONS 1.A TO 1.C

These Example and comparison sticks were made by the following general method M1:

The RI of the selected particulate antiperspirant active was first measured using standard procedures (Becke line method, described supra). The proportions of each of the carrier oils was then determined by calculation (weight averaging their individual RIs and measuring the resultant mixture) such that the RI of the mixture closely matched to that of the selective active. Where necessary, minor adjustment was made to the weight ratio of the oils following the measurement. The gellants G1, G2 and G3 and any other gellants used, were introduced into alcohol oil (C3 or C4) with stirring by an overhead paddle stirrer together with any particulate S4 and the mixture heated until the gellants dissolved. The oils other than C3 or C4 such as C1 or C2 were heated to 50° C. whilst being stirred using a stirrer bar and particulate antiperspirant active (S1, S2 or S3) was introduced slowly. When the entire actives had been added, the mixture was sheared at 50° C. using a Silverson™ mixer at 7000 rpm for 5 minutes. The dispersion of active particulates was heated in an oven at 85° C. whilst stirring continued. The gellant/alcohol solution was allowed to cool to 90° C., and the active/oil mixture was added. The temperature of the resultant mixture was kept constant at 85° C., (except in Ex1.4 at 90° C.) and it was stirred thoroughly and any fragrance was then added. The mixture was allowed to cool and then poured into stick barrels at about 5° C. above the regular solidification temperature of the mixture (obtained by allowing a sample to solidify under quiescent conditions, or from previous trials), and allowed to cool to ambient.

The formulations in parts by weight and the properties of the sticks are summarised in Table 1 below:

Comp Co1.A was a rather soft translucent stick. When applied to skin it left a "wet" oily film that did not disappear.

Comp Co1.B "NB" indicated that G1 solution gelled at 105° C., i.e. before antiperspirant/oil dispersion could be added, so that the desired composition was not made.

Comp Co1.C "NC" indicated that G3 solution gelled at 108° C., i.e. before antiperspirant/oil dispersion could be added, so that the desired composition was not made.

Ex 1.1 was a firm, translucent stick. It applied well to skin leaving no white deposits and a slight oily film which dried/disappeared quickly.

Ex 1.2 was a firm translucent stick. It left no white deposits on skin, but did leave a rather oily film. Stick glide was however very good.

Ex 1.3 was a firm translucent stick. It applied well to skin leaving no white deposits and no oily film.

Ex 1.4 was a firm just translucent stick. It applied well to skin leaving no white deposits and only a slight oily film. Subsequent investigation revealed that the batch of S2 employed had a refractive index of 1.534 instead of the previously assumed 1.530 so that the phases were less closely refractive index matched.

Further compositions according to the present invention can be made by substituting the same amount of cis/trans-1,2-di-dodecanamidocyclohexane for Ajinimoto gellant GP-1 (G2) in any one of Examples 1.1 or 1.3.

EXAMPLES 2.1 to 2.3

These Examples were made in accordance with general method for Example 1 and contained cyclohexane alkyl amide gellants. The formulations in parts by weight and their stick properties are summarised in Table 2 below.

TABLE 2

|  | Ex 2.1 | Ex 2.2 | Ex 2.3 |
|---|---|---|---|
| G1 | 2 | 2 | 2.5 |
| G2 | 2 | 2 |  |

TABLE 1

| | % by weight | | | | | | |
|---|---|---|---|---|---|---|---|
| | Ex 1.1 | Co 1.A | Co 1.B | Ex 1.2 | Co 1.C | Ex 1.3 | Ex 1.4 |
| Constituent | | | | | | | |
| G1 | 2 |  | 5 | 2 |  | 3 | 3 |
| G2 | 3 | 5 |  |  |  | 3 |  |
| G3 |  |  |  | 1 | 3 |  | 1 |
| C1 | 51.87 | 51.87 | 51.87 | 52.5 | 52.5 |  | 51.5 |
| C2 |  |  |  |  |  | 50.0 |  |
| C3 |  |  |  | 19.5 | 19.5 | 18.0 | 18.5 |
| C4 | 18.13 | 18.13 | 18.13 |  |  |  |  |
| S1 | 25 | 25 | 25 | 25 | 25 | 25 |  |
| S2 |  |  |  |  |  |  | 25 |
| F |  |  |  |  |  | 1 | 1 |
| Process Conditions | | | | | | | |
| Pour Temp (° C.) | 75 | 75 | "NB" | 72 | "NC" | 70 | 85 |
| Stick properties | | | | | | | |
| Hardness (mm) | 10.5 | 14.7 |  | 13.7 |  | 11.2 | 13.0 |
| pay-off (g) | 0.64 | 0.79 |  | 0.80 |  | 0.71 | 0.85 |
| whiteness | 15.3 |  |  |  |  |  |  |
| % light | 3.2 | 5.0 |  | 2.1 |  | 1.6 | 0.3 |

TABLE 2-continued

|  | Ex 2.1 | Ex 2.2 | Ex 2.3 |
|---|---|---|---|
| G4 | 1 |  | 2.5 |
| G5 |  | 1 |  |
| C4 | 17.73 | 17.73 | 17.73 |
| C1 | 51.27 | 51.27 | 51.27 |
| S1 | 25 | 25 | 25 |
| F | 1 | 1 | 1 |
| Properties |  |  |  |
| Stick Pour Temp (° C.) | 75 | 70 | 80 |
| Hardness (mm) | 12.7 | 11.7 | 11.8 |
| pay-off (black cotton) (g) | 0.725 | 0.684 | 0.742 |
| % Transmission | 26.7 | 39.3 | 25.0 |

3.1, 3.2 and 3.3 were firm translucent/transparent sticks. They applied well to skin leaving no white deposits and no oily film.

EXAMPLES 3.1 TO 3.5

The Examples were made by the same general method as for Example 1 and employed other carrier oils. The formulations in parts by weight and their properties are summarised in Table 3 below.

TABLE 3

|  | Ex 3.1 | Ex 3.2 | Ex 3.3 | Ex 3.4 | Ex 3.5 |
|---|---|---|---|---|---|
| G1 | 2.5 | 2.5 | 2.5 | 2.5 | 2.5 |
| G2 | 2.5 | 2.5 | 2.5 | 2.5 | 2.5 |
| C4 | 10.62 | 9.18 | 10.28 | 8.77 | 7.19 |
| C1 | 51.03 | 52.47 | 51.37 | 46.03 | 40.76 |
| C5 |  |  | 6.85 | 13.7 | 20.55 |
| C6 |  | 6.85 |  |  |  |
| C7 | 6.85 |  |  |  |  |
| S1 | 25.0 | 25.0 | 25.0 | 25.0 | 25.0 |
| F | 1.0 | 1.0 | 1.0 | 1.0 | 1.0 |
| Properties |  |  |  |  |  |
| Stick Pour Temp (° C.) | 185 | 85 | 82 | 85 | 90 |
| Hardness (mm) | 8.8 | 9.1 | 9.1 | 8.7 | 8.1 |

All sticks were translucent in appearance and left no white residue on skin or clothes.

EXAMPLES 4.1 to 4.5

In these Examples further formulations were made using a second sample of antiperspirant active S2. The formulations expressed in parts by weight and their stick properties are summarised in Table 4 below.

TABLE 4

|  | Ex 4.1 | Ex 4.2 | Ex 4.3 |
|---|---|---|---|
| G1 | 2.75 | 2.75 | 2.5 |
| G2 | 2.75 | 2.75 | 2.5 |
| C4 | 7.14 | 11.82 | 11.40 |
| C1 | 40.47 | 56.2 | 57.6 |
| S4 | 0.5 | 0.5 |  |
| C5 | 20.4 |  |  |
| S3 | 25 | 25 | 25 |
| F |  |  | 1.0 |
| Stick Pour Temp (° C.) | 90 | 85 | 82 |
| Properties |  |  |  |
| Hardness (mm) | 7.2 | 8.8 | 9.5 |
| % Transmission | 4.1 | 8.2 | 17.1 |

All sticks were translucent in appearance and left no white residue on skin or clothes.

EXAMPLES 5.1 AND 5.2

These examples were made in accordance with the general method employing other class (i) gellants. The ingredient are expressed in parts by weight and the formulation properties are summarised in Table 6 below.

Preparative Method for 2-butyloctanoyl Chloride 2-butyloctanoyl chloride was prepared by adding excess oxalyl chloride (50 ml, 2M solution) in dichloromethane (DCM) to the liquid acid Jaric I-12 (7.65 g, 38 mmol) at room temperature, the mixture was stirred for 2 hours at room temperature. The mixture was refluxed for 2 hours, cooled and all dichloromethane and excess oxalyl chloride removed on a rotary evaporator. The resulting crude acid chloride was re-dissolved in dichloromethane solvent and used immediately. In stage 1 below, the amount of L-Glutamic acid dimethyl ester hydrochloride was 9.7 g.

Preparative Method for Gellants G5 and G6

Gellants G5 and G6 were made by a two stage method. In stage 1 the N-acyl L glutamic acid dimethyl ester was formed and in stage 2, this was converted to the corresponding N-acyl L glutamic acid dibutylamide, both stages employing laboratory grade chemicals from Sigma Aldrich except for the 2-butyl octanoyl chloride.

A 250 ml 3 necked round bottomed flask equipped with a magnetic stirrer was charged with L-Glutamic acid dimethyl ester hydrochloride salt (15 g, 71 mmol). Dichloromethane (150 ml, approximately 10 mls per gram of the HCl salt) was then introduced to the flask at laboratory ambient temperature (20° C.) with stirring. Triethylamine (TEA, 8.61 g, 85 mmol) was then added with stirring, whereupon a white precipitate immediately appeared. This mixture was left to stir at room temperature for a period of 60 minutes. A second portion of TEA (7.17 g, 71 mmol) was then added to the reaction mixture together with the respective acid chloride (71 mmol in 50 ml DCM) (2-ethyl-butanoic acid chloride for Ex5.1 and isopentanoic acid chloride for Ex 5.2) whilst maintaining the temperature between 0° C.-10° C. during the addition. The reaction mixture was stirred overnight at ambient temperature.

Next morning, the precipitate was filtered off and a clear filtrate was obtained which was washed successively with dilute hydrochloric acid, saturated sodium bicarbonate solution and water in a separating funnel. Evaporation of all solvent under reduced pressure yielded the corresponding N-Acyl L-Glutamic acid dimethyl ester which was detected to be free from residual acid and starting materials.

In the second stage, the product of stage 1 (typically 10 g, 23-38 mmol) was dissolved in toluene (100 ml, 10 mls per gram of dimethyl ester) then added to a 250 ml reactor vessel equipped with magnetic stirrer, dropping funnel and water condenser. Butylamine in excess (30-50 ml, 300-500 mmol) was then introduced slowly dropwise, after which the reaction solution was heated up to 90° C. and stirred thoroughly. Progress of the conversion from dimethyl ester to diamide was monitored using both RP HPLC and FT-IR on withdrawn samples until no ester was detected any longer or if some ester remained, until the relative intensity of the ester versus the amide infra-red peaks had become constant. The reaction took approximately 24 hours.

When cooled to ambient temperature, the reaction mixture formed a gel which was filtered under vacuum and washed with cold solvent until a crude white solid material was obtained. Residual butylamine was removed by washing the crude product with 25 g acid based Amberlyst A-15™ resin in respectively ethanol for G6 and acetonitrile for G7, followed by filtration through charcoal or a further wash with base resin (Amberlyst A-21™, 25 g) for G6.

TABLE 5

| N-Acyl Derivative | Gellant | Purification Step | Purity (Area %) | M P (° C.) |
|---|---|---|---|---|
| Isopentanoyl | G6 | Acid resin/base resin/ethanol | 98.02 | 194 |
| butyl octanoyl | G7 | Acid Resin/ acetonitrile | N/A | 164 |

TABLE 6

| | Ex 5.1 | Ex 5.2 |
|---|---|---|
| G6 | 2.5 | |
| G7 | | 1.0 |
| G2 | 3.0 | 4.0 |
| C1 | 56.59 | 56.59 |
| C4 | 11.91 | 11.91 |
| S1 | 25.0 | 25.0 |
| F | 1.0 | 1.0 |
| Properties | | |
| Clarity (% Transmission) | 5.5 | 4.9 |
| Hardness (mm penetrometer) | 12.7 | 12.3 |
| Pour Temp | 89 | 74 |

Both sticks were translucent in appearance and left no white deposits on skin.

Measurement of Properties i) Stick Hardness—Penetrometer

The hardness and rigidity of a composition which is a firm solid can be determined by penetrometry. If the composition is a softer solid, this will be observed as a substantial lack of any resistance to the penetrometer probe.

A suitable procedure is to utilises a lab plant PNT penetrometer equipped with a Seta wax needle (weight 2.5 grams) which has a cone angle at the point of the needle specified to be 9°10'+/−15". A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted. Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

ii) Deposition by Firm Sticks (Pay-Off)

A second property of a composition is the amount of it which is delivered onto a surface when the composition is drawn across that surface (representing the application of a stick product to human skin), sometimes called the pay-off. To carry out this test of deposition when the composition is a firm stick, able to sustain its own shape, a sample of the composition with standardised shape and size is fitted to apparatus which draws the sample across a test surface under standardised conditions of temperature and applied pressure a specified number of times (thrice each way). The amount transferred to the surface is determined as an increase in the weight of the substrate to which it is applied. If desired the colour, opacity or clarity of the deposit may subsequently be determined. A specific procedure for such tests of deposition and whiteness applicable to a firm solid stick used apparatus to apply a deposit from a stick onto a substrate under standardised conditions and then measures the mean level of white deposits using image analysis.

The substrates used were 12×28 cm strips of black cotton fabric. The substrates were weighed before use. The sticks were previously unused and with domed top surface unaltered.

The apparatus comprised a flat base to which a flat substrate was attached by a clip at each end. A pillar having a mounting to receive a standard size stick barrel was mounted on an arm that was moveable horizontally across the substrate by means of a pneumatic piston.

Each stick was kept at ambient laboratory temperature overnight before the measurement was made. The stick was advanced to project a measured amount from the barrel. The barrel was then placed in the apparatus and a spring was positioned to bias the stick against the substrate with a standardised force (500 g load). The apparatus was operated to pass the stick 120 mm laterally across the substrate six times with a final velocity of 140 mm/s.

The substrate was carefully removed from the rig and reweighed. The whiteness of the deposit could subsequently be measured as described at (v) below.

(iii) Whiteness of Deposit

The deposits from the at test (ii) above, were assessed for their whiteness after an interval of 24 hours approximately.

This was carried out using a KS Image Analyser fitted with a Sony XC77 monochrome video camera with a Cosmicar 16 mm focal length lens positioned vertically above a black table illuminated from a high angle using fluorescent tubes to remove shadowing. The apparatus was initially calibrated using a reference white card, after the fluorescent tubes had been turned on for long enough to give a steady light output. A cloth with a deposit thereon from the previous test was placed on the table and the camera was used to capture an image. An area of the image of the deposit was selected and analysed using KS400™ image software. This notionally divided the image into a large array of pixels and measured the grey level of each pixel on a scale of 0 (black) to 255 (white). The average of the grey intensity was calculated and can be compared with the background reading for the cloth of 10. This was a starting point to measure the whiteness of the deposit, with higher numbers indicating a whiter deposit. It was assumed that low numbers show a clear deposit allowing the substrate colour to be seen.

(iv) Clarity of Formulation—Light Transmission

The translucency of a composition may be measured by placing a sample of standardised thickness in the light path of a spectrophotometer and measuring transmittance, as a percentage of light transmitted in the absence of the gel.

This test was carried out using a dual-beam Perkin Elmer Lambda 40 spectrophotometer. The sample of composition was poured hot into a 4.5 ml cuvette made of poly(methylmethacrylate) (PMMA) and allowed to cool to an ambient temperature of 20-25° C. Such a cuvette gives a 1 cm thickness of composition. Measurement was carried out at 580 nm, with an identical but empty cuvette in the reference beam of the spectrophotometer, after the sample in the cuvette had been held for 24 hours. A transmittance measured at any temperature in the range from 20-25° C. is usually adequately accurate, but measurement is made at 25° C. if more precision is required.

(v) HPLC Method for Purity of Gellant

Purity of the gellant was measured by reverse phase HPLC with UV detection.

A mobile phase was prepared comprising a 300 ml aliquot of deionised water, to which was added a 700 ml aliquot of HPLC grade acetonitrile and 1.0 ml of trifluoroacetic acid (Aldrich™ spectrophotometric grade), all solvents were then mixed thoroughly and degassed. 0.001 g of sample was weighed into a 2 ml HPLC vial and made up to volume with the mobile phase.

The sample was then analysed using a Hewlett Packard 1050 HPLC System™ equipped with a Hypersil ODS 5 μm $C_{18}$, 250×4.6 mm ID column, HP Autosampler™ and UV Diode Array Detector set to 210 nm.

Analysis was carried out under the following conditions:

| | |
|---|---|
| Isocratic/gradient: | Isocratic |
| Flow rate: | 1.2 ml/minute |
| Run time: | 10 minutes |
| Temperature: | Ambient |
| Injection volume: | 20 μl |

All results are quoted in area percent.

The invention claimed is:

1. A solid cosmetic composition comprising a water-immiscible liquid, a cosmetic active suspended therein and a solidifying amount of a gellant for the water-immiscible liquid, wherein the gellant for the water-immiscible liquid comprises a combination of gellant (i), an N-acyl substituted amino acid amide of formula $A^X$—CO—$R^X$ in which $A^X$ represents the residue of an amino acid amide and $R^X$ represents a branched alkyl group containing from 4 to 12 carbon atoms and gellant (ii), a fibre-forming amido structurant selected from:—
   (iia) an N-acyl substituted amino acid amide other than gellant (i)
   (iib) a cyclodipeptide which satisfies the following general formula:

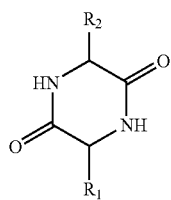

in which one of $R_1$ and $R_2$ represents an alkyl, alkyl ester group and the other represents an alkyl or alkaryl group and
   (iic) 1,2-amido substituted cyclohexane substituted each amido substituent having formula
   —$(CH_2)_v$—NH—CO—$R^{111}$ in which $R^{111}$ represents an alkyl group of from 5 to 27 Carbon atoms and v is an integer selected from zero and one in an effective relative weight ratio of gellants (i) and (ii) and the composition is at least translucent.

2. A composition according to claim 1 wherein $A^X$ represents the residue of diamido-substituted glutamic acid or aspartic acid.

3. A composition according to claim 2 wherein $A^X$ represents the residue of diamido-substituted glutamic acid.

4. A composition according to claim 1 wherein each amido substituent in $A^X$ has the formula —CO—NH—$R^Z$ in which $R^Z$ represents an alkyl group containing from 3 to 6 carbon atoms.

5. A composition according to claim 4 wherein $R^Z$ represents a linear alkyl group.

6. A composition according to claim 4 wherein $R^Z$ represents butyl.

7. A composition according to claim 1 wherein $R^X$ contains 4 to 8 carbon atoms.

8. A composition according to claim 7 wherein $R^X$ contains 7 or 8 carbon atoms.

9. A composition according to claim 1 wherein $R^X$ contains a single side chain.

10. A composition according to claim 9 wherein the side chain contains up to 4 carbon atoms.

11. A composition according to claim 1 wherein —CO—$R^X$ is the residue of 2-ethyl-hexanoic acid.

12. A composition according to claim 1 in which gellant (i) is present in a concentration of from 0.75 to 8% by weight of the composition.

13. A composition according to claim 12 in which gellant (i) is present in a concentration of at least 1.5% by weight of the composition.

14. A composition according to claim 1 in which gellant (i) is present in a concentration of from 1 to 15% by weight of the water-immiscible oils.

15. A composition according to claim 14 in which gellant (i) is present in a concentration of at least 2% by weight of the water-immiscible oils.

16. A composition according to claim 1 wherein gellant (iia) is an N-acyl substituted amino acid amide of formula $A^Y$—CO—$R^Y$ in which $A^Y$ represents an amino acid amide and $R^Y$ represents a linear alkyl group containing from 9 to 21 carbon atoms.

17. A composition according to claim 16 wherein the weight ratio of gellant (i) to gellant (iia) is selected in the range of from 4.5:1 to 1:4.5.

18. A composition according to claim 17 wherein the weight ratio of gellant (i) to gellant (iia) is selected in the range of from 3:1 to 1:3.

19. A composition according to claim 18 wherein the weight ratio of gellant (i) to gellant (iia) is selected in the range of from 2:1 to 1:2.

20. A composition according to claim 16 wherein $R^Y$ represents undecanyl.

21. A composition according to claim 16 wherein $A^Y$ represents the residue of diamido-substituted glutamic acid.

22. A composition according to claim 16 wherein each amido substituent in $A^Y$ has the formula —CO—NH—$R^Z$ in which $R^Z$ represents an alkyl group containing from 3 to 6 carbon atoms.

23. A composition according to claim 16 wherein $R^Z$ represents a linear alkyl group.

24. A composition according to claim 22 wherein $R^z$ represents butyl.

25. A composition according to claim 16 wherein the proportion of N-acyl amino acid amide gellant (iia) is from 1.5 to 8% by weight of the composition.

26. A composition according to claim 16 wherein the proportion of N-acyl amino acid amide gellant (iia) is from 2 to 15% by weight of the water-immiscible oils.

27. A composition according to claim 16 in which the combined weight of gellant (i) and N-acyl aminoacid amide gellant (ii) is from 2.5 to 8% of the composition.

28. A composition according to claim 27 wherein the combined weight of gellant (i) and gellant (iia) is from 4 to 7% of the composition.

29. A composition according to claim 1 wherein the cyclodipeptide satisfies the formula:—

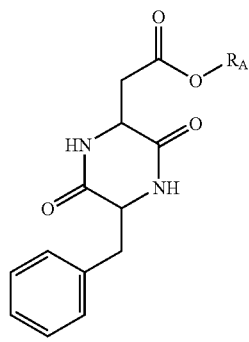

in which $R_A$ represents a carbocyclic or heterocyclic group containing not more than 2 rings.

30. A composition according to claim 29 wherein $R_A$ represents a 6 membered carbocyclic ring that is optionally substituted by 1 to 3 alkyl groups, each independently containing 1 to 3 carbon atoms.

31. A composition according to claim 30 wherein the residue RA is derivable from thymol or a 3,5-dialkylcyclohexanol.

32. A composition according to claim 1 wherein the cyclodipeptide gellant (iib) is present in a weight ratio to the gellant (i) of from 1:5 to 1:1.

33. A composition according to claim 32 wherein the cyclodipeptide gellant (iib) is present in a weight ratio to the gellant (i) of from 1:4 to 1:1.5.

34. A composition according to claim 33 wherein the cyclodipeptide gellant (iib) is present in a weight ratio to the gellant (i) of from 1:3 to 1:2.

35. A composition according to claim 1 wherein the cyclodipeptide gellant (iib) is present in an amount of from 0.4 to 4% by weight of the composition.

36. A composition according to claim 1 wherein the cyclodipeptide gellant (ii) is present in an amount of from 0.8 to 8% by weight of the water-immiscible oils.

37. A composition according to claim 1 wherein the combined weight of gellant (i) and cyclodipeptide gellant (iib) is from 2% to 8% of the composition.

38. A composition according to claim 37 wherein the combined weight of gellant (i) and cyclodipeptide gellant (iib) is from 2.5% to 5% of the composition.

39. A composition according to claim 1 wherein in the formula for gellant (iic) v=zero.

40. A composition according to claim 1 wherein the amido-substituted gellant (iic) is present in a weight ratio to the gellant (i) of from 1:3 to 3:1.

41. A composition according to claim 1 wherein the amido-substituted gellant (iic) is present in an amount of from 1 to 8% by weight of the composition.

42. A composition according to claim 1 wherein the water-immiscible oil comprises a silicone oil.

43. A composition according to claim 42 wherein the silicone oil is present in a proportion of from 30 to 80% by weight of the water-immiscible carrier oils.

44. A composition according to claim 43 wherein the silicone oil comprises a non-volatile silicone oil, having a refractive index of at least 1.50.

45. A composition according to claim 1 wherein the continuous phase comprises a water-immiscible monohydric alcohol having a melting point of not higher than 30° C. and a boiling point of higher than 100° C.

46. A composition according to claim 45 wherein the alcohol is a branched aliphatic alcohol containing from 12 to 22 carbon atoms.

47. A composition according to claim 45 wherein the monohydric alcohol is present in a proportion of from 20 to 50% by weight of the water-immiscible liquid and preferably from 25 to 40%.

48. A composition according to claim 1 wherein a benzoic acid ester is present in a proportion of from 0.5 to 50% by weight the water-immiscible liquid.

49. A composition according to claim 48 wherein the weight proportion benzoic acid ester in the water-immiscible liquid is from 5 to 30%.

50. A composition according to claim 48 wherein from 0.1 to 4%, preferably 0.5 to 2% by weight of the water-immiscible liquid is benzyl benzoate.

51. A composition according to claim 1 wherein the antiperspirant or deodorant active comprises an astringent aluminium and/or zirconium salt.

52. A composition according to claim 51 wherein the aluminium or zirconium salt comprises an aluminium chlorohydrate, an aluminium-zirconium chlorohydrate or an aluminium-zirconium chlorohydrate complex.

53. A composition according to claim 1 wherein the antiperspirant active is present in a weight proportion of from 5 to 40% of the composition.

54. A process for the preparation of an at least translucent antiperspirant stick comprising the steps of:—
  a. forming a mobile mixture of (i) a liquid phase comprising a water-immiscible oil, (ii) a gellant therefor and (iii) a suspended particulate antiperspirant or deodorant by
  a1. mixing the liquid phase with the gellant,
  a2. heating the liquid phase to a temperature at which the gellant dissolves
  a3. Introducing the particulate antiperspirant or deodorant active into the liquid phase either before or after dissolution of the gellant
  b. matching the refractive index of the particulate antiperspirant or deodorant with the refractive index of the liquid phase, by
  b1. selecting the water-immiscible oil or a combination of such oils such that the refractive index of the liquid phase matches the refractive index of the particulate antiperspirant or deodorant optionally after adjustment of the combination and/or
  b2. previously adjusting the refractive index of the particulate antiperspirant or deodorant to match its refractive index with that of the liquid phase
  c. introducing the mobile mixture into a dispensing container and
  d. cooling or allowing the mobile mixture to cool to a temperature at which it sets wherein the gellant comprises gellant (i) and gellant (ii) as described in claim 1.

55. A process according to claim 54 wherein at least one of gellants (i) and (ii) are dissolved in a first fraction of the water-immiscible liquid and the antiperspirant or deodorant active is suspended in a second fraction of the water-immiscible liquid and the first fraction is then mixed with the second fraction.

56. A process according to claim 55 wherein the first fraction of liquid comprises a water-immiscible monohydric alcohol that is liquid at 20° C. and boils at above 100° C.

57. A cosmetic method for inhibiting or controlling perspiration and/or malodour generation comprising applying topically to human skin an effective amount of a cosmetic composition according to claim 1.

* * * * *